United States Patent [19]
Wolf et al.

[11] Patent Number: 5,230,624
[45] Date of Patent: Jul. 27, 1993

[54] WATER PURIFICATION SYSTEM FOR DENTAL INSTRUMENT

[76] Inventors: Leo H. Wolf, 1209 Golf View Dr.; Mark F. Wolf, 498 County Trunk Hwy. M, both of River Falls, Wis. 54032

[21] Appl. No.: 973,454

[22] Filed: Nov. 9, 1992

[51] Int. Cl.⁵ .................................. A61C 1/10
[52] U.S. Cl. .......................... 433/82; 433/88
[58] Field of Search .............. 433/80, 81, 82, 84, 433/85, 86, 87, 88

[56] References Cited

U.S. PATENT DOCUMENTS

| | | | |
|---|---|---|---|
| 3,593,423 | 7/1971 | Jones | 433/80 |
| 3,698,088 | 10/1972 | Austin, Jr. | 433/80 |
| 3,772,189 | 11/1973 | Kreusch et al. | 210/753 |
| 3,817,860 | 6/1974 | Lambert et al. | 210/753 |
| 3,923,665 | 12/1975 | Lambert et al. | 210/501 |
| 4,059,522 | 11/1977 | Polley et al. | 210/753 |
| 4,190,529 | 2/1980 | Hatch | 210/753 |
| 4,238,477 | 12/1980 | Lambert et al. | 424/79 |
| 4,741,697 | 5/1988 | Herbison | 433/80 |
| 4,888,118 | 12/1989 | Barnes et al. | 210/753 |
| 4,950,159 | 8/1990 | Hansen | 433/80 |
| 4,961,698 | 10/1990 | Vlock | 433/88 |
| 4,973,247 | 11/1990 | Varnes et al. | 433/82 |
| 4,978,297 | 12/1990 | Vlock | 433/88 |
| 4,999,190 | 3/1991 | Fina et al. | 424/79 |
| 5,024,600 | 6/1991 | Kline | 433/82 |
| 5,026,359 | 6/1991 | Burroughs | 210/501 |

OTHER PUBLICATIONS

"Water Conditioning & Purification" publication entitled MCV Resin: Iodination Based on Space Technology, Mar., 1992.

Primary Examiner—John J. Wilson
Attorney, Agent, or Firm—Burd, Bartz & Gutenkauf

[57] ABSTRACT

A system for purifying water supplied to a dynamic dental instrument has a disposable element having an iodinated resin containing a polyiodide, $I_5$. Disease causing microorganisms in water flowing through the element are neutralized with neutralizing agents released directly into the microorganisms when the microorganisms come into contact with the resin. Residual iodine is released as water passes through the resin and remains between the element and the dynamic instrument to maintain dental unit water purity.

22 Claims, 2 Drawing Sheets

FIG. 1
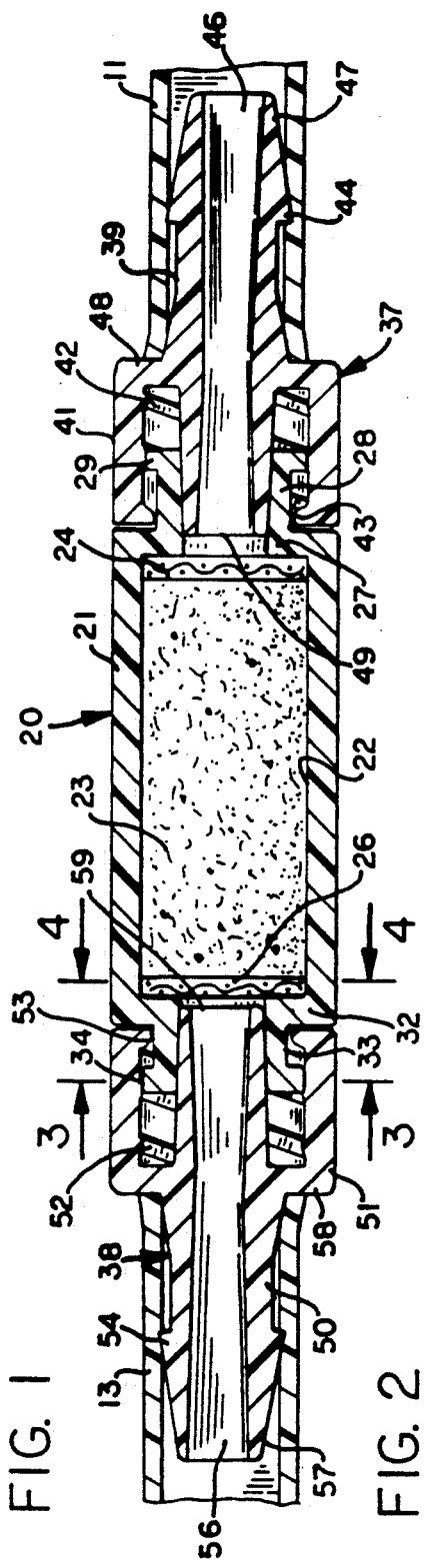
FIG. 2
FIG. 3
FIG. 4

WATER PURIFICATION SYSTEM FOR DENTAL INSTRUMENT

FIELD OF THE INVENTION

The invention relates to modern dental units containing a water supply system that provides coolant and rinse water to the highspeed dental handpiece, ultrasonic scaler and air/water syringe.

BACKGROUND OF THE INVENTION

All modern dental units have a water supply that provides coolant and rinse water to the dynamic dental instruments including the high-speed handpiece, air/water syringe and ultrasonic scaler. This water supply is connected to a domestic water system. Microbiological studies of this water supply revealed that the water is contaminated by water organisms and oral flora. These organisms have been found to be massive in number and some identified as pathogenic. Dental researchists have stated that this contamination could cause infection in immuno-suppressed patients, and cross infection may occur between dental patients.

Clinical tests show that oral flora is aspirated from a patient's oral cavity into the dental unit water lumens through the dynamic dental instruments. This revelation has prompted the Centers of Disease Control to recommend a 20 to 30 second purge of these instruments between each patient appointment. The American Dental Association and The American National Standards Institute developed Specification Number 47, dated Apr. 12, 1984, as the manufacturing criterion for dental unit manufacturers. This specification requires that a means be incorporated in the dental unit to prevent water from being drawn back beyond the point of the dental instrument connection. These are attempts to improve the quality of water used for dental treatment. However, continuing research indicates that neither has significatly reduced contamination.

Medical studies have determined that disease incubation periods vary. Because of this variance it is difficult to make accurate assessments as to the time and place of infection. Dental treatment is frequently subgingival and invasive of the mucosa therefore providing a direct access to the vascular system. It is therefore prudent to use microbiologically pure water for cooling and rinsing during dental treatment in lieu of water considered by public health standards to be polluted and nonpotable.

SUMMARY OF THE INVENTION

The invention is directed to a water purification apparatus used to maintain dental unit water quality.

The apparatus incorporates a quick connect cartridge in the water lumen of a dynamic dental instrument tubing. The cartridge contains a polyiodide $I_5$ purification resin that neutralizes and kills disease causing bacteria, virus and protozoa by means of demand-release electrostatic attraction as water flows through the cartridge. The resin has a positive charge and the microorganisms are negatively charged whereby the microorganisms are attracted to the resin. When contact is made between the resin and the microorganism, an appropriate amount of iodine is released from the resin directly into the organism to neutralize the organism. A residual iodine is also released from the resin as the water passes through the resin and remains in the water between the cartridge and the dynamic instrument. As the instrument is used aspirated oral flora are killed by the residual iodine. This maintains a microbiologically pure water condition reducing cross infection potential and preventing disease transmission by way of the dental unit water. Quick releasable lock structures are used to connect opposite ends of the cartridge to the water carrying tubes. At the beginning of each work day, the cartridge is change on each water lumen of the dental unit to maintain microbiologically pure water conditions for that work day period.

DESCRIPTION OF DRAWING

FIG. 1 is a side elevational view of a dental handpiece, partly sectioned attached to a water supply line including a water disinfectant element or cartridge;

FIG. 2 is an enlarged sectional view taken along the line 2—2 of FIG. 1;

FIG. 3 is a sectional view taken along the line 3—3 of FIG. 2;

FIG. 4 is a sectional view taken along the line 4—4 of FIG. 2;

DESCRIPTION OF THE PREFERRED EMBODIMENT

Figure 6:
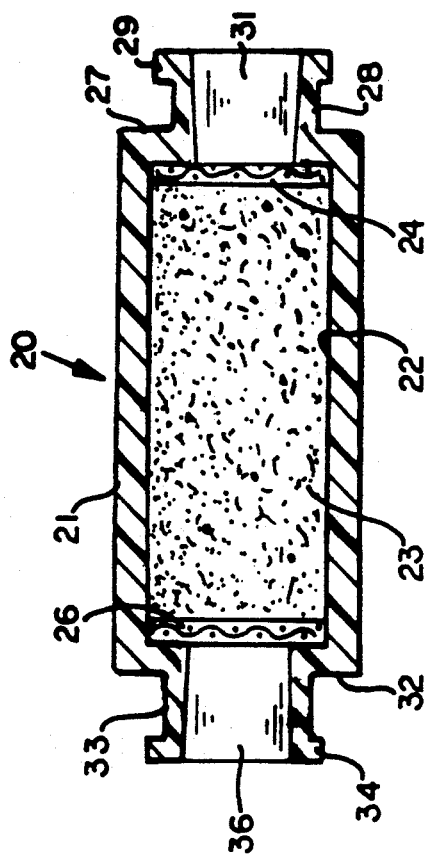
FIG. 6 is a top plan view of the cartridge.

Referring to FIG. 1, there is shown a dental instrument 10 having a water intake tube 13 and an air tube 12. Dental instrument 10 is shown as a dental handpiece. Dental handpiece 10 can also be an air/water syringe or ultrasonic scaler. A water supply tube 11 leading to dental handpiece 10 includes a water purification and disinfectant element or cartridge of the invention, indicated generally at 20. Cartridge 20 is located in the water line between water tubes 11 and 13. Releasable quick connect lock structures or fittings 37 and 38 mounted on the ends of tubes 11 and 13 are used to connect opposite ends of cartridge 20 to tubes 11, 13. Cartridge 20 cleans and disinfects water passing through the cartridge and supplies a residual disinfectant to the water that remains in the water as it moves between cartridge 20 and dental handpiece 10. The residual disinfectant neutralizes water contaminants that may be drawn back into the water system for dental handpiece 10.

Referring to FIGS. 2 to 7, cartridge 20 is a generally cylindrical member having a housing 21 surrounding a tubular chamber 22. Cartridge 20 is manufactured to retrofit the tubings of modern dental units. Cartridge chamber 22 contains a resin or filter material 23, as seen in FIGS. 2 and 6, that functions to purify and release residual disinfectant into water passing through cartridge 20. This ensures that water spray 14 discharged from handpiece 10 is in a pure condition and contains a disinfectant thereby reducing the potential of cross infection between dental patients and preventing disease transmission via the dental instrument water system.

For example, filter material 23 can be a purification resin containing the polyiodide, $I_5$ as disclosed by Lambert and Fina in U.S. Pat. No. 4,238,477, and Fina, Lambert and Bridges in U.S. Pat. No. 4,999,190. As water flows through cartridge 20, the resin neutralizes and extinguishes disease causing bacteria, virus, protozoa and other microorganisms that may be present in water by means of a demand-release process. The demand-release process is a result of the natural process of electrostatic attraction. The resin has a positive charge and the microorganisms are negatively charged causing the microorganisms to be attracted to the resin. When a microorganism contacts the resin an appropriate amount of iodine is released from the resin directly into the microorganism effectively neutralizing the microorganism. The resin also releases a residual iodine into the water as the water passes through cartridge 20. The iodine remains as a residual in the water line between cartridge 20 and dental handpiece 10. Aspirated oral flora and other contaminants are destroyed by the residual iodine in the water. This maintains a microbiologically pure water condition and prevents disease transmission through the handpiece water system with subsequent use of handpiece 10. Other types of resins and neutralizing agents can be used as filter material 23 for cartridge 20.

Figure 5:
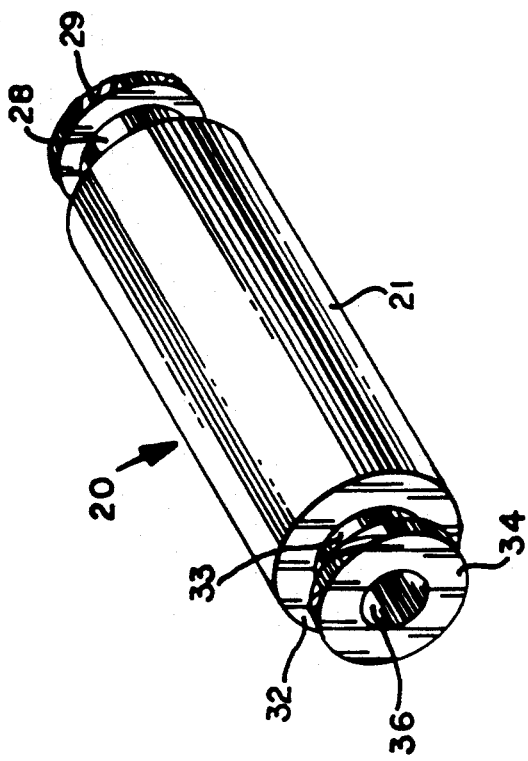
FIG. 5 is a perspective view of the cartridge.
Figure 7:
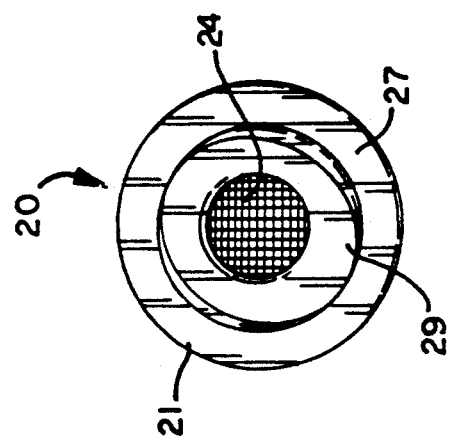
FIG. 7 is an end view of the cartridge, the opposite end being a mirror image thereof.

Filter material 23 is held within chamber 22 by a pair of transverse porous members 24 and 26 located at opposite ends of chamber 22. Porous members 24 and 26 have a circular shape with a plurality of relatively small openings in the form of a mesh or screen, as seen in FIGS. 4 and 7, to allow passage of water through cartridge 20 while retaining filter material 23 within chamber 22. Other shapes and opening patterns may be used to construct porous members 24 and 26. Porous members 24 and 26 have a tight fit relationship with the inside surface of housing 21. Housing 21 has end walls 27 and 32 located adjacent the outer peripheral surfaces of porous members 24, 26, respectively. End wall 27 has a centrally located passage 31 surrounded by an outwardly extended tubular collar 28. The diameter of passage 31 is less than the diameter of porous member 24. Water enters cartridge 20 through passage 31 from water supply tube 11 and flows through porous member 24 and filter material 23 for purification. The outer end of collar 28 has an annular flange 29 with a threaded outer surface, as shown in FIG. 5, that cooperates with a threaded fitting 37 to releasably connect end 27 of cartridge 20 to water supply tube 11.

Similarly, end wall 32 of cartridge 20 has a central passage 36 surrounded by an outwardly extended tubular collar 33. The diameter of porous member 26 is greater than the diameter of passage 33. Water enters cartridge 20 through passage 31 from water supply tube 11, flows through porous member 24 and filter material 23 and then out porous member 26 and passage 36 into water intake tube 13 connected to dental instrument 10. Water flowing through passage 36 is in a microbiologically purified condition and contains a residual disinfectant that remains in water spray 14 to destroy aspirated oral flora and other contaminants that may be drawn back into the dental unit water system. The outer end of collar 33 has an annular flange 34 with a threaded outer surface, as shown in FIG. 5, that cooperates with a second threaded fitting 38 to releasably connect cartridge 20 with water intake tube 13.

Ends 27 and 32 of cartridge 20 are substantially the same and are interchangeable whereby either end 27, 32 of cartridge 20 can be connected to water supply tube 11 or water intake tube 13 and vice versa. For example, when end 32 is attached to water supply tube 11 and end 27 is attached to water intake tube 13, water flows into cartridge 20 through passage 36 and moves out of the cartridge through passage 31. This eliminates the necessity of an alignment procedure during installation of cartridge 20 in instrument 10.

Referring to FIG. 2, fitting 37 has a generally tubular body 39 having an internal passage 46. A ring 41 surrounding inner end 49 of body 39 has an inwardly directed wall 48 attached to body 39. Collar 28 of cartridge 20 telescopes into ring 41 and surrounds inner end 49 of body 39. The inside surface of ring 41 has threads 42 that accommodate threads on the outer surface of flange 29 to releasably hold fitting 37 on cartridge 20. The outer end of ring 41 has an inwardly projecting lip 43 that engages the outer surface of collar 28. The top surface of lip 43 is located adjacent end wall 27 of cartridge 20 when the outer threaded surface of flange 29 is tightly threaded on threads 42 of fitting 37. Inner end 49 of body 39 is located in passage 31. End 49 is slightly tapered to facilitate insertion thereof into passage 31.

As shown in FIG. 2, the outer diameter of body 39 increases to a diameter that is substantially the same as the diameter of passage 31. This prevents water from leaking between water supply line 11 and cartridge 20. Outer end 47 of body 39 is inserted into the passage of water supply tube 11. End 47 has a tapered outer surface to facilitate insertion of end 47 into the passage of water supply tube 11. Fitting 37 has a foot 44 located adjacent end 47 to prevent fitting 37 from inadvertantly slipping out of water supply tube 11. The outer surface of body 39 diverges outwardly to form foot 44. The diameter of foot 44 is slightly larger than the diameter of the passage in water supply tube 11 thereby expanding water supply tube 11 when body 39 is located in the tube passage to provide holding action. The middle portion of body 39 also diverges outwardly to an increased diameter, as seen in FIG. 2, to provide additional holding action. The end of water supply tube 11 engages wall 48 when fitting 37 is fully inserted into the passage of water supply tube 11.

Fitting 38 has substantially the same structure as fitting 37. Fitting 38 has a tubular body 50 with an internal passage 56. A ring 51 surrounds inner end 59 of body 50. Ring 51 has an inwardly directed wall 58 secured to body 50. Collar 33 of cartridge 20 telescopes into ring 51 and surrounds inner end 59 of body 50. The inside surface of ring 51 has a plurality of threads 52 that accommodate threads on the outer surface of flange 34 to releasably hold fitting 38 on cartridge 20. Ring 51 has a lip 53 that engages the outer surface of collar 33. The top surface of lip 53 is located adjacent end wall 32 of cartridge 20 when the outer threaded surface of flange 34 is tightly threaded on threads 52 of fitting 38. Ends 57 and 59 of body 50 have tapered outer surfaces to facilitate insertion thereof into the passage of water intake tube 13 and cartridge passage 36, respectively. Fitting 38 has a foot 54 located adjacent end 57 that engages the lumen of water intake tube 13 to prevent fitting 38 from inadvertently slipping out of water intake tube 13, as seen in FIG. 2.

In use, cartridge 20 is inserted between water supply tube 11 and water intake tube 13 in the water line leading to dental handpiece 10. Fittings 37 and 38 mounted on the ends of tubes 11 and 13 releasably lock opposite ends of cartridge 20 onto the ends of tubes 11 and 13. Outer threaded surfaces of cartridge flanges 29 and 34 engage threaded inner surfaces 42 and 52 of fitings 37 and 38 to releasably hold cartridge on water tubes 11 and 13. Cartridge 20 contains filter material 23 that purifies and adds residual disinfectant to water supplied to dental handpiece 10. The residual disinfectant destroys contaminants and disease causing microorganisms when they are drawn back into the water line. This maintains a microbiologically pure water system for dental handpiece 10 preventing cross infection between dental patients. Porous cartridge members 24 and 26 contained within chamber 22 of cartridge 20 prevent passage of filter material 23 from cartridge 20.

At the beginning of each work day the cartridge 20 is changed. The threaded surfaces of cartridge flanges 29 and 34 and threaded fitting surfaces 42 and 52 are separated to quickly remove cartridge 20 from fittings 37 and 38 secured to tubes 11 and 13. Cartridge 20 is discarded and then the opposite ends of a new cartridge can be quickly connected to fittings 37 and 38. This maintains a microbiologically pure water condition and prevents cross-contamination during subsequent use of handpiece 10.

While there has been shown and described a preferred embodiment of the water purification apparatus, it is understood that changes in materials and structures can be made by those skilled in the art without departing from the invention. The invention is defined in the following claims.

We claim:

1. A dental apparatus having a fluid supply system comprising: a dental instrument having first tube means, second tube means providing fluid to the first tube means, fluid purification means releasably mounted on the first tube means and the second tube means, the fluid purification means including filter means operable to purify and supply disinfectant means to the fluid as the fluid passes through the filter means, the disinfectant means remaining as a residual in the fluid as the fluid moves between the fluid purification means and the dental instrument whereby when the fluid is discharged from the dental instrument the fluid is in a microbiologically pure condition and contains the disinfectant means, the disinfectant means neutralizing contaminants drawn back into the fluid supply system to prevent cross infection, and means connected to the first tube means and second tube means to releasably attach the fluid purification means to the first and second tube means.

2. The apparatus of claim 1 wherein: the fluid purification means has chamber means in communication with the first tube means and second tube means, the filter means located in the chamber means, the means connected to the first tube means and second tube means having passages open to the chamber means.

3. The apparatus of claim 1 wherein: the fluid purification means has coupling means releasably accommodated by the means connected to the first tube means and second tube means.

4. The apparatus of claim 1 wherein: the fluid purification means has porous means adjacent ends of the filter means to retain the filter means in the fluid purification means and allow fluid to flow through the fluid purification means.

5. The apparatus of claim 1 wherein: the fluid purification means comprises a cartridge having a housing defining a chamber, the housing having opposite ends, each end having a passage open to the chamber, the filter means located in the chamber.

6. The apparatus of claim 5 wherein: the cartridge has collar means attached to the end, the collar means cooperating with the means connected to the first tube means and second tube means to releasably attach the cartridge to the first and second tube means.

7. The apparatus of claim 1 wherein: the fluid purification means includes collar means cooperating with the means connected to the first tube means and second tube means to releasably attach the fluid purification means to the first and second tube means.

8. The apparatus of claim 1 wherein: the filter means is an iodinated resin.

9. The apparatus of claim 8 wherein: the resin contains a polyiodide $I_5$.

10. The apparatus of claim 1 wherein: the disinfectant means is a residual iodine released into the fluid as the fluid passes through the filter means.

11. A cartridge located in a water line leading to a dental instrument having a water supply system comprising: a housing defining an internal chamber, filter means located in the chamber operable to purify and release a disinfectant into water flowing through the chamber, the disinfectant remaining as a residual in the water as the water moves between the cartridge and the dental instrument whereby when the water is discharged from the dental instrument the water is in a microbiolobically pure condition and contains the disinfectant, the disinfectant neutralizing contaminants drawn back into the water supply system to prevent cross infection, and coupling means attached to the housing for releasably connecting the cartridge to the water line leading to the dental instrument.

12. The cartridge of claim 11 including: porous means located in the chamber adjacent ends of the filter means to retain the filter means in the chamber and allow water to flow through the chamber.

13. The cartridge of claim 11 wherein: the housing has opposite ends, each having a passage open to the chamber, the coupling means located adjacent the passage.

14. The cartridge of claim 13 including: a porous means adjacent ends of the filter means and passages, each passage having a diameter less than a diameter of the porous means.

15. The cartridge of claim 11 wherein: the coupling means comprises a pair of tubular collars attached to opposite ends of the housing, each collar having a threaded outer surface to releasably connect the cartridge to the water line.

16. The cartridge of claim 11 wherein: the filter means comprises an iodinated resin.

17. The cartridge of claim 11 wherein: the filter means is a resin containing a polyiodide $I_5$.

18. The cartridge of claim 11 wherein: the disinfectant is a residual iodine released into the water as the water passes through the filter means.

19. A cartridge for purifying water supplied from a water supply system to a dental instrument comprising: a housing defining an internal chamber, the housing having opposite ends, each end having a passage open to the chamber, filter means located in the chamber operable to purify and release disinfectant means into water flowing through the filter means, porous means located in the chamber adjacent ends of the filter means to retain the filter means in the chamber and allow water to flow through the chamber, and coupling means secured to the end of the housing used to releasably connect the cartridge to the water supply line of the dental instrument.

20. The cartridge of claim 19 wherein: the filter means comprises an iodinated resin.

21. The cartridge of claim 19 wherein: the filter means is a resin containing a polyiodide $I_5$.

22. The cartridge of claim 19 wherein: the disinfectant means is iodine remaining as a residual in the water as the water moves between the cartridge and the dental instrument whereby when the water is discharged from the dental instrument the water contains the residual iodine to neutralize contaminants drawn back into the water supply system and prevent cross infection.

* * * * *